US005744145A

United States Patent [19]
Bertoli et al.

[11] Patent Number: 5,744,145
[45] Date of Patent: Apr. 28, 1998

[54] PREPARATION OF LIPID COMPOSITIONS FOR COSMETIC PRODUCTS

[75] Inventors: Constantin Bertoli, Romanel S/Lausanne; Umberto Bracco, Vevey; Angiolino Delvecchio, Taverne; Armand Malnoe, Givrins, all of Switzerland

[73] Assignee: Nestec S.A., Vevey, Switzerland

[21] Appl. No.: 540,311

[22] Filed: Oct. 6, 1995

[30] Foreign Application Priority Data

Nov. 5, 1994 [EP] European Pat. Off. ............. 94117482

[51] Int. Cl.[6] ............... A61K 7/00; A23D 5/00; C11B 3/14
[52] U.S. Cl. ............... 424/401; 426/417; 426/476; 426/488; 426/487; 426/492; 426/601; 260/420; 260/428
[58] Field of Search ............... 424/401; 426/417, 426/476, 488, 487, 492, 601; 260/420, 428; 514/844

[56] References Cited

U.S. PATENT DOCUMENTS

| | | | |
|---|---|---|---|
| 4,416,901 | 11/1983 | Bochskandl | 424/363 |
| 4,454,159 | 6/1984 | Musher | 424/358 |
| 4,526,793 | 7/1985 | Ingenbleek | 426/72 |
| 4,874,629 | 10/1989 | Chang et al. | 426/601 |
| 4,883,659 | 11/1989 | Goodman | 424/78 |
| 4,996,072 | 2/1991 | Marschner et al. | 424/417 |

FOREIGN PATENT DOCUMENTS

| | | |
|---|---|---|
| 0477825 | 4/1992 | European Pat. Off. . |
| 0581624 | 2/1994 | European Pat. Off. . |

*Primary Examiner*—Gollamudi S. Kishore
*Attorney, Agent, or Firm*—Vogt & O'Donnell, LLP

[57] ABSTRACT

Oil mixtures, which provide lipid compositions for restraining skin degeneration, contain, by weight, 30% to 50% rice bran oil and 15% to 25% sesame oil and also contain additional oil, which includes in particular, oil from among maize oil, wheat germ oil and sunflower oil, so that the composition contains linoleic acid and contains vitamin E for protecting the composition against oxidation, the composition being prepared from oils containing gum, color and odor which are subjected to degumming, decoloring and deodorizing, the deodorizing being carried out under conditions of temperature and vacuum so that the composition has at least 2% by weight unsaponifiable oil matter and particularly from 2% to 3% unsaponifiable oil matter.

13 Claims, No Drawings

PREPARATION OF LIPID COMPOSITIONS FOR COSMETIC PRODUCTS

BACKGROUND OF THE INVENTION

The present invention concerns a lipid composition intended to be used in cosmetic compositions, in particular a lipid composition having an anti-ageing action.

Premature ageing of the epidermis is partly due to external attack such as for example from UV radiation and pollution generating free radicals.

It is known, for example from European Patent Application Publication No. 0477825, that sesame oil has the property of stabilizing edible vegetable oils rich in unsaturated fatty acids, for example maize oil, against oxidation.

The anti-radical properties of unsaponifiable fractions of sesame oil and wheat germ oil in cosmetic compositions are also known, for example from European Patent Application Publication No. 0581624.

SUMMARY OF THE INVENTION

The object of the present invention is to provide a lipid composition for cosmetic products having an anti-ageing action on the skin, namely an anti-radical, soothing and hydrating action, while being naturally stabilized against oxidation, namely not containing added anti-oxidants.

To that end, lipid compositions of the present invention for cosmetic products or for cosmetic purpose are based upon a mixture of oils which provide anti-ageing action, maintain good hydration at the epidermis and have anti-radical properties, and the oils employed are rich in anti-oxidant unsaponifiable compounds.

The invention also provides processes for preparation of the lipid compositions, in which raw or partially refined oils are used, characterized in that the mixture of oils is degummed, decolorized and deodorized, wherein the deodorization is carried out under conditions enabling obtaining a content of at least 2% by weight, and in particular, a content 2% to 3% by weight, of unsaponifiable matter, as well as stability against oxidation corresponding to an induction period of at least 15 h in the RANCIMAT test at 100° C.

The lipid composition according to the invention is characterized in that it comprises a mixture of oils which comprise, in particular, rice bran oil and sesame oil and in that it comprises at least 2% by weight unsaponifiable matter, and in particular, from 2% to 3% by weight of unsaponifiable matter, and in that the fatty acids of the triglycerides comprise, by weight, 30% to 40% of oleic acid, 40% to 50% of linoleic acid and less than 2% of alpha-linolenic acid.

DETAILED DESCRIPTION OF THE INVENTION

The composition of the present invention contains rice bran oil which is particularly rich in gamma-oryzanol which has anti-oxidant activity.

The composition also contains sesame oil, certain constituents of which specifically inhibit delta 5 desaturase, the enzyme responsible for the biotransformation of dihomogamma-linolenic acid (DHGLA) into arachidonic acid (AA). It is thus likely to have an anti-inflammatory action, in as much as the formation of products derived from AA, such as, for example, leucotriene B4, which is pro-inflammatory, should profitably reduce products derived from DHGLA, for example prostaglandins of series 1 having an anti-inflammatory action.

The composition contains an oil comprising an appreciable quantity of oleic acid which has a structuring action and acts as a vehicle for essential bio-active fatty acids while being neutral from the point of view of bioactivity. The oleic acid content gives the lipid mixture good stability to oxidation and photo-oxidation, which prevents the formation of active oxygenated radicals.

The oils of choice meeting these requirements are preferably rice bran oil and sesame oil. The oils in question preferably constitute 45% to 65%, for example 60%, by weight of the final lipid mixture.

The composition contains oils providing essential fatty acids of the n-6 family, low n-3 fatty acids, so as to take account of the greater biochemical reactivity of those of the n-3 family.

Oils rich in fatty acids of the n-6 family are selected from those rich in linoleic acid, for example maize oil, wheat germ oil, sunflower oil or blackcurrant seed oil. Thus the composition has a high linoleic acid content, with 40% to 50% by weight of fatty acids. This acid is a constituent of ceramides which play an important role as a barrier against dehydration of the epidermis. Linoleic acid also shows itself to be active against cellular hyperproliferation associated with lack of essential fatty acids, an effect that could be associated with the re-establishment of normal levels of series 2 prostaglandins in the epidermis.

These "active" fatty acids can also be incorporated in the formulation in the form of their ethyl or propionic esters, in quantities calculated so as to obtain the desired relative levels and proportions.

The composition according to the invention also contains an oil rich in vitamin E which can improve its keeping properties, for example a wheat germ oil.

The average composition in fatty acids of the triglycerides in the final composition is as follows:

| Fatty acids | % by weight | | % by weight |
| --- | --- | --- | --- |
| C16:0 | 10–15 | preferably | <13.5 |
| C16:1,n-7 | 0.05–0.5 | " | <0.3 |
| C18:0 | 1–4 | " | <3 |
| C18:1,n-9 | 30–50 | " | <35 |
| C18:2,n-6 | 40–60 | " | <48 |
| C18:3,n-3 (alpha) | 1–2 | " | <2 |
| C20:0 | <1 | " | <0.5 |
| C20:1 | <1 | " | <0.5 |

On the basis of their respective compositions in fatty acids and in natural anti-oxidant constituents, the following mixtures of oils are preferred:

| Oil | % by weight | | % by weight |
| --- | --- | --- | --- |
| Rice bran oil | 30–40 | preferably | 40 |
| Maize oil | 20–40 | " | 30 |
| Sesame oil | 15–25 | " | 20 |
| Wheat germ oil | 5–15 | " | 10 |

According to the processes of the present invention, a cold-pressed sesame oil is preferably used, which contains the desired compounds sesamoline and sesamine. Wheat germ and sesame oils are preferably chosen that are low in lecithins and rich in unsaponifiable matter.

Degumming preferably takes place by putting the mixture of oils in contact with a concentrated solution of citric acid, in the presence of water at about 80° C., during which hydration is carried out, followed by separation of the gums, for example by centrifuging or decanting.

In a variant of the degumming treatment, the mixture of oils heated to 80° C. is treated by circulating steam under vacuum.

After separation of the gums, as indicated previously, the mixture of degummed oils is treated by putting it into contact with an adsorbent consisting of damp amorphous silica gel for about 20 min at 80°–85° C. under a vacuum of about 50–80 mbar.

In certain cases, bleaching is also carried out with decolorizing earth activated with acid.

Finally, the mixture of oils is deodorized under controlled conditions, for example at about 180° C. with about 1% live steam and under a vacuum of about 1–2 mbar for about 2 h. It is thus possible to maintain an appreciable content of unsaponifiable matter and in particular to control the tocopherols.

The lipid composition according to the invention may be advantageously used in various aqueous or anhydrous cosmetic compositions for treatment of the skin, such as fluids, creams and lotions for the face, hands and body, sun creams and lotions, antiwrinkle creams and lotions and similar compositions.

The cosmetic composition in question can be, in particular, in the form of a solution, a water-in-oil emulsion or an oil-in-water emulsion, a suspension or an aerosol. As anhydrous cosmetic compositions incorporating the lipid composition according to the invention, reference may be made to body oils, anhydrous balms, anti-sun oils and lipsticks.

In such a cosmetic composition, the lipid composition according to the invention may represent 1 to 80%, preferably 5 to 60% by weight.

Such a cosmetic composition generally includes, in suitable quantities, additives such as, for example emulsifiers, anti-perspirant agents, stabilizers, preservatives, sun filters, perfumes, dyes or emollients, waxes, pearl agents and inorganic or organic fillers.

The lipid composition according to the invention may also be used for a cosmetic purpose in the form of a nutritional supplement, for example in capsules or gelatin capsules.

EXAMPLES

The following examples illustrate the invention. In these, percentages and parts are given by weight except where indicated to the contrary.

Examples 1–3
Preparation of the mixture of oils

The following partially refined oils were mixed with stirring and under nitrogen in the proportions indicated.

| Oil | % |
|---|---|
| Rice bran oil | 40 |
| Maize oil | 30 |
| Sesame oil | 20 |
| Wheat germ oil | 10 |

In order to do this, the oils were mixed in the proportions indicated above in a stainless steel reactor provided with a double walled system with fluid circulation to keep the temperature constant and a variable speed stirrer, avoiding temperatures greater than 30° C.

Example 1

The mixture was then heated to 65° C. and treated with 0.3% of 50% citric acid, 2 to 3% water was added and the precipitated gums were separated off by centrifuging.

The degummed mixture was then put into contact with 1% hydrated amorphous silica gel (TRISYL) and 0.5% hydrated amorphous silica gel (TRISYL 300) at 80°–85° C. for 20 min under a vacuum of 50–80 mbar.

The mixture was finally deodorized at 180° C. for 3 hours by steam entrainment with 1% of steam per hour.

The properties of the final mixture of refined oils were as follows:

| | |
|---|---|
| LOVIBOND colour, 2.5 cm (1") cell, R | 0.9 |
| LOVIBOND colour, 2.5 cm (1") cell, Y | 5.3 |
| Induction time, RANCIMAT test, h | 17.5 |
| Unsaponifiable matter content, measured by IUPAC method 2.104, g/kg | 21.3 |
| Free fatty acid content, % | 0.28 |

Example 2

The procedure was as in the preceding Example 1, apart from the fact that the preliminary degumming was carried out by steam treatment at 80° C. for 20 min with 2% steam. The results of the LOVIBOND colour analyses and the RANCIMAT test were identical.

Example 3

The procedure was as in Example 2, except that the degummed mixture was put into contact with 0.5% of TRISYL 300 hydrated amorphous silica gel and that following this treatment the mixture was put in contact with 0.25% of TONSIL OPTIMUM FF decolorizing earth before deodorization. The coloration and the induction time results were as follows:

| | |
|---|---|
| LOVIBOND colour, 2.5 cm (1") cell, R | 1.4 |
| LOVIBOND colour, 2.5 cm (1") cell, Y | 9.5 |
| Induction time, RANCIMAT test, h | 16.5 |

Example 4

| Anhydrous balm | |
|---|---|
| Ingredients | % |
| Lanolin | 35 |
| Hydrogenated lanolin | 30 |
| Ozokerite | 3 |
| Lipid composition according to Example 2 | 20 |
| Cyclopentadimethylsiloxane | 12 |

The anhydrous product of this Example was obtained by mixing the constituents at 70° C., and then cooling with stirring until room temperature was reached.

Example 5

| Ingredients | % |
|---|---|
| Fatty alcohol esters $C_8$–$C_{10}$ | 26 |
| Ozokerite | 10 |
| Carnauba wax | 3 |
| Bees wax | 3 |
| Pigment | 9 |
| Perfume | 0.1 |
| Castor oil | qsp 100 |
| Lipid composition of Example 2 | 6 |

The pigments were sieved. The constituents were then mixed at 70° C., except for the perfume. The mixture was left to cool to 35° C. with stirring and the perfume was then added. The preparation was finally transferred to a triple roll mill.

Example 6

Make-up foundation

| Ingredients | % |
|---|---|
| Lipid composition of Example 2 | 4 |
| Mixture of glyceryl mono-di-stearate, stearic acid and glycerine (40/50/5/5) | 3.3 |
| Mixture of lanolin alcohol and liquid paraffin (15/85) | 3 |
| Glyceryl mono-di-iso-stearate | 1.8 |
| Isopropyl palmitate | 5 |
| ethyl-2-hexyl palmitate | 5 |
| Titanium oxide | 8.31 |
| Brown iron oxide | 0.73 |
| Yellow iron oxide | 1.7 |
| Black iron oxide | 0.26 |
| Propyl p-hydroxybenzoate | 0.1 |
| Methyl p-hydroxybenzoate | 0.1 |
| Perfume | 0.3 |
| Triethanolamine | 1.2 |
| Hydrated magnesium aluminium silicate | 1.5 |
| Sodium carboxymethylcellulose | 0.14 |
| Cyclopentadimethylsiloxane | 8 |
| Glycerine | 3 |
| Sterilized demineralized water | qsp 100 |
| Propylene glycol | 3 |
| Stearic acid | 2.4 |

The pigments were blended and sieved and they were then incorporated in the oily phase, previously warmed to 70° C. The sodium carboxymethylcellulose was dispersed separately in water. When the solution was homogeneous, the other components of the aqueous phase were added and the mixture was heated to 75° C. The two phases were then emulsified with rapid homogenization. The emulsion was then allowed to cool with stirring, the perfume and triethanolamine were added at 35° C. and homogenization was then carried out. The preparation was then transferred to a triple roll mill.

Example 7

Moisturising protective body lotion

| Ingredients | % |
|---|---|
| Polysorbate 60 | 0.8 |
| Perfume | 0.3 |
| Glycerol stearate and PEG 100 stearate | 1 |

—continued

Moisturising protective body lotion

| Ingredients | % |
|---|---|
| Hydrogenated polyisobutene | 2 |
| Lipid composition of Example 2 | 8 |
| Stearic acid | 1 |
| Glycerine | 3 |
| CARBOPOL 941 | 0.3 |
| Triethanolamine | 0.3 |
| Water + preservative | qsp 100 |

The CARBOPOL 941 was dispersed in water. When the solution was homogeneous, the other components of the aqueous phase were added and the mixture was heated to 75° C. The constituents of the oily phase were mixed separately at 70° C. The two phases were then emulsified with rapid homogenization. The mixture was allowed to cool with stirring and the perfume, triethanolamine and preservative were added at 35° C., followed by homogenization. The preparation was allowed to cool to room temperature and packaged.

Example 8

Protective care fluid

| Ingredients | % |
|---|---|
| Methyl glucose sesquistearate | 2 |
| Lipid composition of Example 2 | 2 |
| Cyclomethicone | 13 |
| Perfume | 0.2 |
| PEG 20 methyl glucose sesquistearate | 2 |
| Xanthan gum | 0.2 |
| Polyacrylamide acid and $C_{13}$–$C_{14}$-isoparaffin and laureth 7 | 0.8 |
| Water + preservatives | qsp 100 |

The xanthan gum was dispersed in water at 75° C. The constituents of the oily phase were mixed separately at 70° C. The two phases were then emulsified under rapid homogenization. The mixture was allowed to cool with stirring, the perfume and preservative was added at 35° C. and homogenization was then carried out. The preparation was then allowed to cool to room temperature and packaged.

Example 9

Protective care cream, oil-in-water emulsion

| Ingredients | % |
|---|---|
| PEG 20 stearate | 1 |
| Glyceryl stearate and PEG 100 Stearate | 1 |
| Stearic acid | 1 |
| Stearyl alcohol | 2 |
| Lipid composition of Example 2 | 20 |
| Soya protein hydrolysate | 0.2 |
| Glycerine | 3 |
| CARBOPOL 941 | 0.4 |
| Triethanolamine | 0.4 |
| Water + preservative | qsp 100 |

The CARBOPOL 941 was dispersed in water. When the solution was homogeneous, the other components of the aqueous phase were added and the mixture was heated to 70° C. The constituents of the oily phase were mixed separately at 75° C. Emulsification of the two phases was then carried out under rapid homogenization. The mixture was then allowed to cool with stirring and the perfume was added at 35° C., followed by homogenization. The preparation was allowed to cool to room temperature and packaged.

Example 10

| Care cream, water-in-oil emulsion | |
|---|---|
| Ingredients | % |
| Sorbitan monoisostearate | 5 |
| Microcrystalline wax | 1 |
| Lipid composition of Example 2 | 19 |
| Fatty acid esters in C$_8$–C$_{10}$ and fatty alcohol esters in C$_{12}$–C$_{18}$ | 1 |
| Modified Montmorillonite gel and neutral oil (triglycerides of caprylic and capric acids) | 5 |
| Propylene glycol | 3 |
| Water + preservative | qsp 100 |

The constituents of the oily phase were mixed at 75° C. The constituents of the aqueous phase were mixed separately at 70° C. After emulsification of the two phases with rapid homogenization, the mixture was allowed to cool with stirring to room temperature and packaged.

We claim:

1. A process for preparation of a lipid composition comprising preparing a mixture of oils which contain gum, color and odor and wherein the oil mixture comprises rice bran oil and sesame oil and comprises additional oil which comprises oil selected from the group consisting of maize oil, wheat germ oil and sunflower oil so that the oil mixture prepared contains linoleic acid and vitamin E, degumming the prepared oil mixture to obtain a first treated oil mixture, decoloring the first treated oil mixture to obtain a second treated oil mixture and deodorizing the second treated oil mixture to obtain a third treated oil mixture, and wherein the oil mixture is prepared, degummed, decolored and deodorized so that the third treated oil mixture comprises, by weight, from 30% to 50% rice bran oil and from 15% to 25% sesame oil and contains the vitamin E for protecting the oil mixture against oxidation and wherein the second treated oil mixture is deodorized under conditions of temperature and vacuum so that the third treated oil mixture comprises at least 2% by weight unsaponifiable oil matter.

2. A process according to claim 1 wherein the additional oil comprises maize oil and wheat germ oil and the oil mixture is prepared, degummed, decolored and deodorized so that the third treated oil mixture comprises, by weight, the maize oil in an amount of from 20% to 40% and the wheat germ oil in an amount of from 5% to 15%.

3. A process according to claim 1 wherein the oil mixture prepared further comprises blackcurrant seed oil.

4. A process according to claim 1 or 2 wherein the oil mixture is prepared, degummed and decolored and the second treated oil mixture is deodorized so that the third oil mixture comprises from 2% to 3% unsaponifiable oil matter.

5. A process according to claim 1 wherein the oil mixture is prepared, degummed, decolored and deodorized so that the third oil mixture comprises, by weight, from 30% to 40% oleic acid, from 40% to 50% linoleic acid and less than 2% alpha-linoleic acid.

6. A process according to claim 1 wherein the second treated oil mixture is deodorized with about 1% live steam and at a temperature of about 180° C. and under a vacuum of about 1 mbar to about 2 mbar for about 2 h to obtain the third treated oil mixture.

7. A process according to claim 1 wherein the degumming comprises contacting the prepared oil mixture with a solution of citric acid in the presence of water to obtain hydrated gum and separating the hydrated gum from the prepared oil mixture to obtain the first treated oil mixture.

8. A process according to claim 7 wherein the separating is carried out by a procedure selected from the group consisting of centrifuging and decanting.

9. A process according to claim 7 wherein the prepared oil mixture and citric acid solution have a temperature of about 80° C.

10. A process according to claim 1 wherein the degumming comprises circulating steam at a temperature of about 80° C. and under vacuum for treating the prepared oil mixture to obtain the first treated oil mixture.

11. A process according to claim 1 wherein the decoloring comprises contacting the first treated oil mixture with hydrated amorphous silica gel at a temperature of from 80° C. to 85° C. under a vacuum of about 50 mbar to about 80 mbar for about 20 mins to obtain the second treated oil mixtures.

12. A process according to claim 1 wherein, the decoloring comprises contacting the first treated oil mixture with hydrated amorphous silica gel at a temperature of from 80° C. to 85° C. under vacuum of about 50 mbar to about 80 mbar for about 20 min and then bleaching the silica-treated mixture with decolorizing earth activated with acid to obtain the second treated oil mixture.

13. A process according to claim 1 wherein the degumming comprises contacting the prepared oil mixture with a solution of citric acid in the presence of water to obtain hydrated gum and separating the hydrated gum from the prepared oil mixture to obtain the first treated oil mixture, wherein the decoloring comprises contacting the first treated oil mixture with hydrated amorphous silica gel at a temperature of from 80° C. to 85° C. under a vacuum of about 50 mbar to about 80 mbar for about 20 mins and wherein the second treated oil mixture is deodorized with about 1% live steam and at a temperature of about 180° C. and under a vacuum of about 1 mbar to about 2 mbar for about 2 h.

* * * * *